US00PP23336P2

(12) United States Plant Patent
Brazelton et al.

(10) Patent No.: US PP23,336 P2
(45) Date of Patent: Jan. 22, 2013

(54) BLUEBERRY PLANT NAMED 'ZF06-079'

(50) Latin Name: *Vaccinium corymbosum*
Varietal Denomination: ZF06-079

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 0 days.

(21) Appl. No.: 13/199,999

(22) Filed: Sep. 14, 2011

(51) Int. Cl.
*A01H 5/00* (2006.01)

(52) U.S. Cl. ..... Plt./157

(58) Field of Classification Search ..... Plt./157
See application file for complete search history.

(56) References Cited

U.S. PATENT DOCUMENTS

PP19,381 P2 10/2008 Lyrene

*Primary Examiner* — Annette Para
(74) *Attorney, Agent, or Firm* — Davis Wright Tremaine LLP; Dale C. Hunt; Wenhua Yu

(57) ABSTRACT

The new blueberry plant variety 'ZF06-079' is provided. 'ZF06-079' is an ornamental variety intended for nursery, landscape, and home garden use. The plant has striking blue/green foliage with pink new growth throughout spring and summer and turns an attractive lavender color in the fall. The new variety ripens in mid-July in Oregon and produces mildly sweet berries in loose clusters. The plant is vigorous, with an estimated chilling requirement of 500 hours.

5 Drawing Sheets

Latin name of the family, genus, and species: Family—Ericaceae. Genus—*Vaccinium*. Species—*corymbosum*.

Variety denomination: The new blueberry plant claimed is of the variety denominated 'ZF06-079'.

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry hybrid known as a *Vaccinium corymbosum* hybrid and referred to as 'ZF06-079', as herein described and illustrated.

The new blueberry plant variety 'ZF06-079' was selected in Lowell, Oreg., in 2006. 'ZF06-079' is an ornamental variety intended for nursery, landscape, and home garden use. The new variety has striking blue/green foliage with pink new growth throughout spring and summer and turns an attractive lavender color in the fall. The new variety ripens in mid-July and produces mildly sweet berries in loose clusters. The plant is vigorous, with an estimated chilling requirement of 500 hours.

The new blueberry plant originated from a cross of 'Toro' (female parent, unpatented) by 'FLX-2' (pollen parent, U.S. Plant Pat. No. 19,381). The female parent was produced by a cross between 'Earliblue' (unpatented) and 'Ivanhoe' (unpatented). The pollen parent was produced by a cross between 'FL92-9' (unpatented) and 'Sunshineblue' (unpatented). The new blueberry plant variety 'ZF06-079' has been planted in replicated trials since 2007.

The new variety differs from the unpatented female parent 'Toro' in that 'ZF06-079' has smaller leaves, is smaller in size, and has pronounced pink and red new growth.

'ZF06-079' differs from the patented male parent 'FLX-2' in that 'ZF06-079' is smaller in size and has more pronounced pink and red new growth.

The new blueberry plant variety 'ZF06-079' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'ZF06-079' has not been observed under all possible environmental conditions. The phenotype may vary somewhat with variations in environment and cultural practices, such as temperature and light intensity, without any variance in genotype.

The following traits have been repeatedly observed in Lowell, Oreg., and are determined to be the unique characteristics of the new blueberry plant variety 'ZF06-079':

1. Striking blue/green foliage with pink new growth;
2. Lavender fall foliage;
3. Compact growth habit.

BRIEF DESCRIPTION OF THE DRAWINGS

The accompanying photographic illustrations show, in full color, typical specimens of the foliage and fruit of the new variety 'ZF06-079'. The colors are as nearly true as is reasonably possible in a color representation of this type.

BOTANICAL DESCRIPTION

Figure 1:
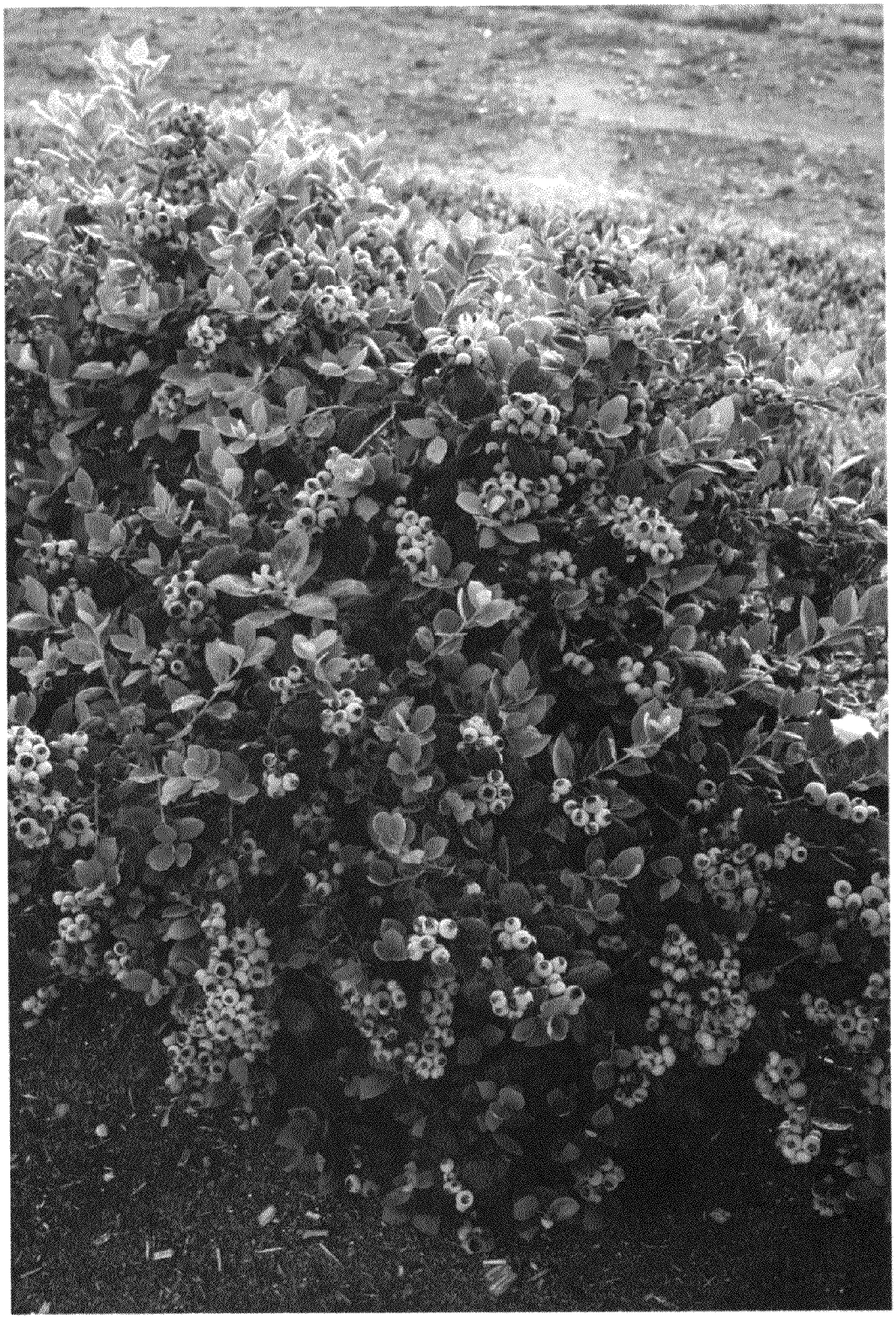
FIG. 1 is a photograph of the new variety 'ZF06-079', demonstrating the plant's compact growth habit.
Figure 2:
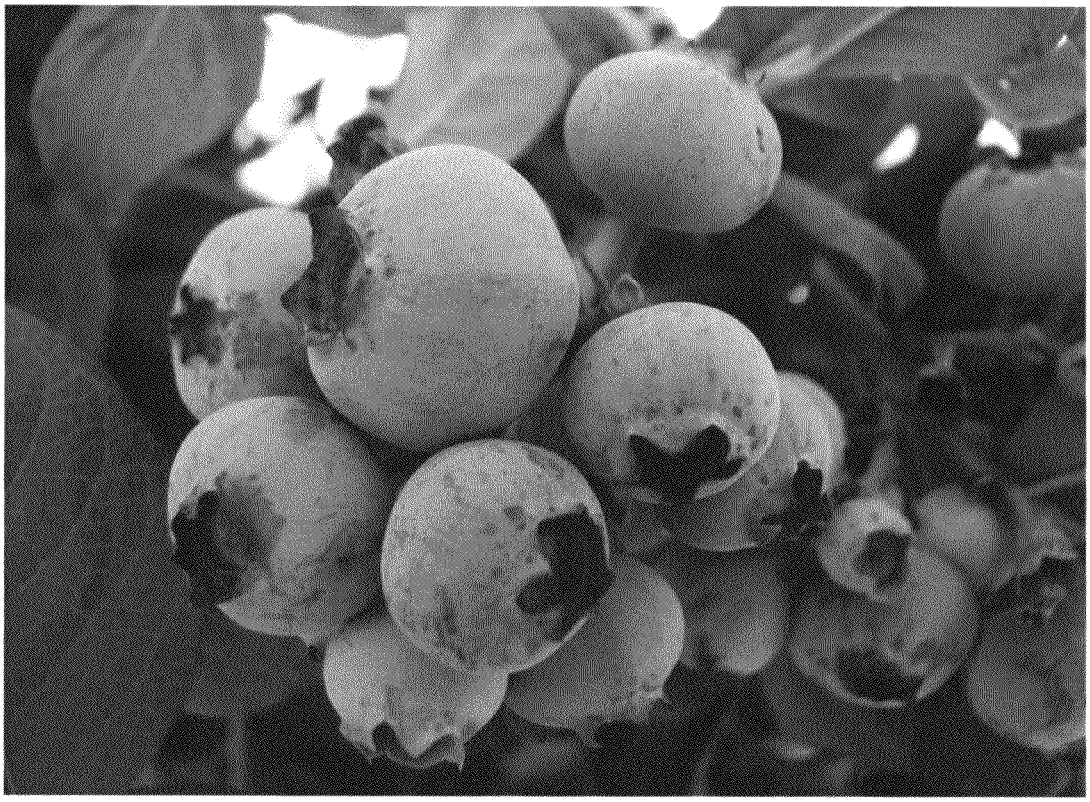
FIG. 2 is a photograph of the fruit of the new variety 'ZF06-079'.
Figure 3:
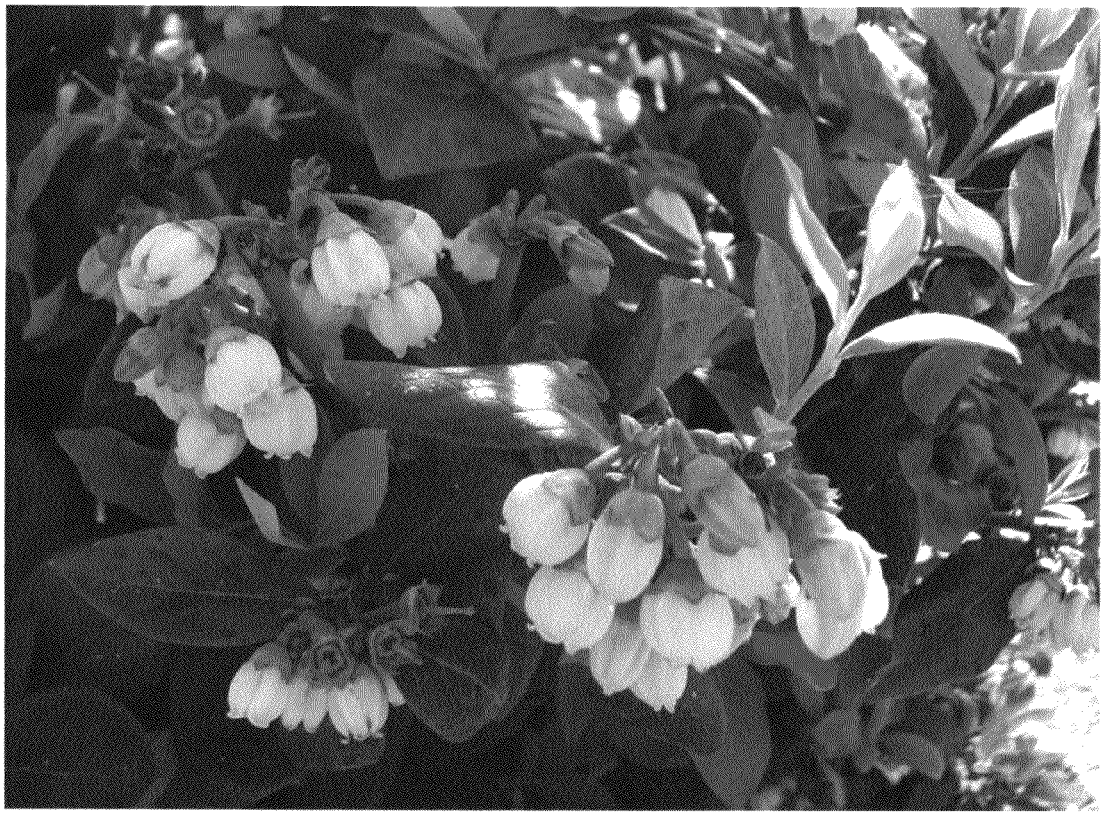
FIG. 3 is a photograph of the flowers of the new variety 'ZF06-079'.
Figure 4:
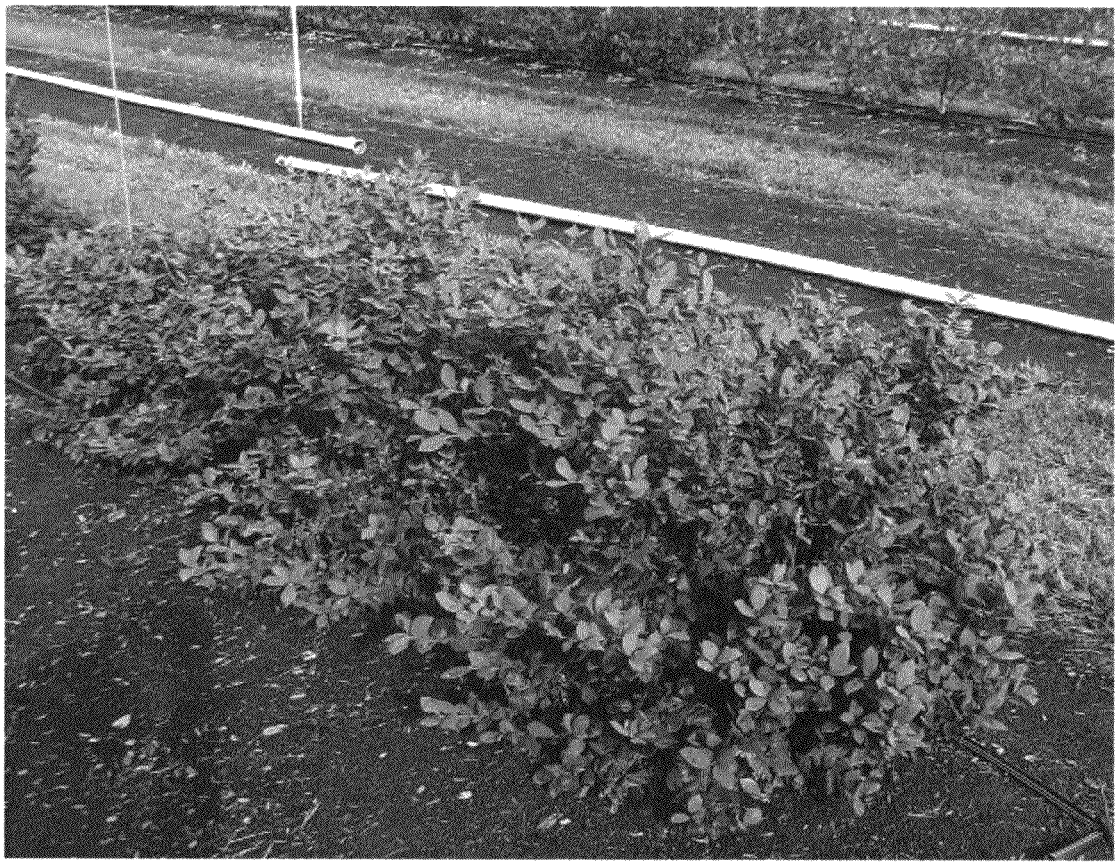
FIG. 4 is a photograph of the fall foliage of the new variety 'ZF06-079'.
Figure 5:
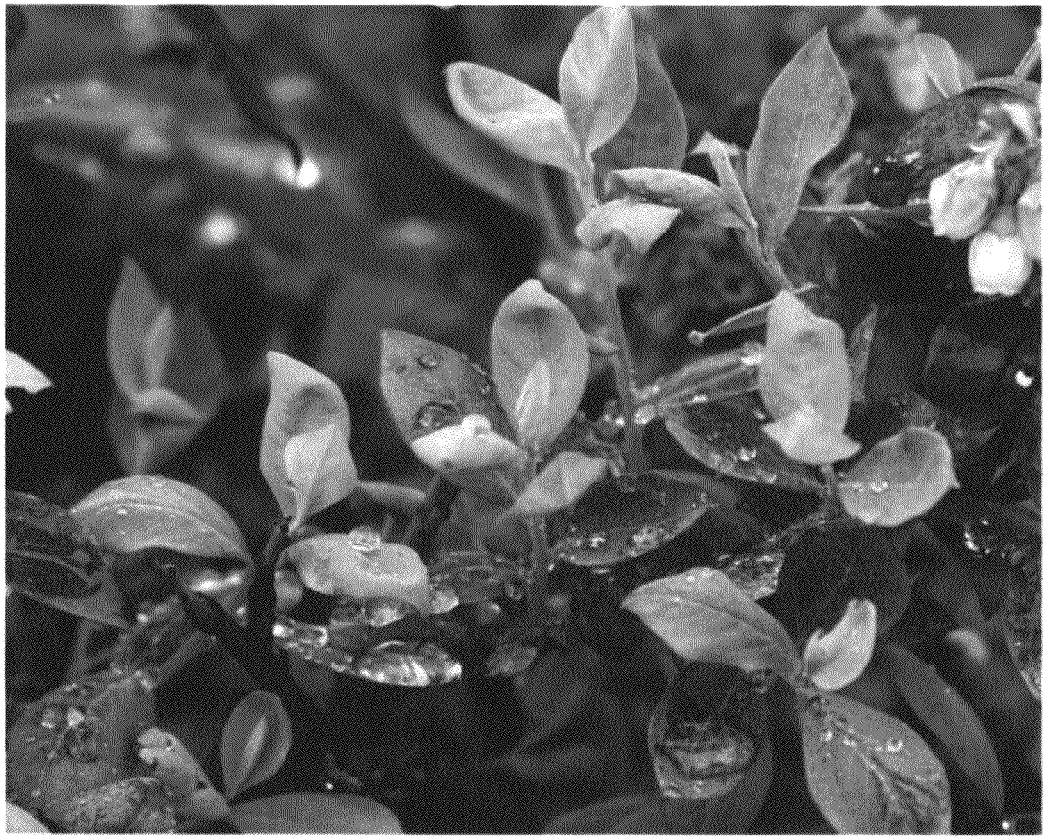
FIG. 5 is a photograph of pink new growth on the variety 'ZF06-079'.

The following detailed description sets forth the distinctive characteristics of 'ZF06-079'. The data which define these characteristics were collected from asexual reproductions of the original selection. Dimensions, sizes, colors, and other characteristics are approximations and averages set forth as accurately as possible. The plant history was taken on plants approximately three years of age, and the descriptions relate to plants grown in the field in Lowell, Oreg. Color designations are from The Pantone Book of Color (by Leatrice Eiseman and Lawrence Herbert; Harry N. Abrams, Inc., Publishers, New York, 1990). Where the Pantone color designations differ from the colors in the photographs, the Pantone colors are accurate.

Classification:
- *a. Family.*—Ericaceae.
- *b. Genus.*—*Vaccinium.*
- *c. Species.*—*corymbosum.*
- *d. Common name.*—Highbush blueberry.

Parentage:
- *Female parent.*—Toro (unpatented).
- *Male parent.*—FLX-2 (U.S. Plant Pat. No. 19,381).

Market class: 'ZF06-079' is an ornamental blueberry variety intended for the nursery, landscape, and home gardening market.

PLANT

Plant size: Medium-sized.
- *a. Height of plant.*—Average of 30 inches (about 76 cm).
- *b. Canopy diameter.*—Average of 24 inches (about 61 cm).

Growth habit: Compact and round.

Plant vigor: Good, produces an average of 6 new canes per year.

Twigginess: Low.

Suckering: Low.

Evergreenness: Evergreen in Lowell, Oreg.

Chilling requirement: Approximately 500 hours of temperatures at or below 45° F. (about 7° C.).

Cold hardiness: Expected range of adaptability USDA hardiness zones 6-8.

Productivity: In Lowell, Oreg., the average per plant harvest weight on 3-year-old plants is 4 lbs (about 1.8 kg).

Propagation: Easy to propagate from softwood cuttings.

Disease resistance/susceptibility:
- *a. Phytophthora.*—Does not appear to be overly susceptible.
- *b. Stem blight.*—Does not appear to be overly susceptible.
- *c. Cane canker.*—Does not appear to be overly susceptible.
- *d. Leaf spot.*—Does not appear to be overly susceptible.
- *e. Bud mites.*—Does not appear to be overly susceptible.

Survival: Good. Plants survive and grow well in both nursery and field settings.

TRUNK AND BRANCHES

Surface texture:
- *a. Surface texture new wood.*—Smooth.
- *b. Surface texture* 1-*year wood.*—Smooth.
- *c. Surface texture* 3-*year and older wood.*—Smooth turning to rough on older wood.

Color:
- *a. Color new wood.*—Pantone Pale Star 12-0626.
- *b. Color* 1-*year wood.*—Pantone Mellow Green 12-0426.
- *c. Color* 3-*year and older wood.*—Pantone Aztec 18-1130, Pantone Gray Sand 13-1010, and Pantone Green Oasis 15-0538.

FOLIAGE

Internode length: Average of 19.7 mm.

Leaf dimensions:
- *a. Leaf length.*—Average of 52 mm.
- *b. Leaf width.*—Average of 30 mm.

Leaf shape: Elliptical, with acute apex and base.

Leaf margin: Entire.

Leaf color upper leaf surface:
- *a. New leaf color.*—Apex of some leaves is Pantone Mellow Green 12-0426, turning to various shades of red and pink (Pantone Poinsetta 17-1654, Pantone Crushed Berry 18-1418, and Pantone Holly Berry 17-1633).
- *b. Mature leaf color.*—Pantone Elm Green 18-0121.

Leaf color lower leaf surface: Pantone Epsom 17-0324.

Pubescence:
- *a. Pubescence upper leaf surface.*—Absent.
- *b. Pubescence lower leaf surface.*—Absent.
- *c. Pubescence leaf margins.*—Absent.

Precocity: Flowers appear before new vegetative growth in Lowell, Oreg.

Petiole:
- *a. Petiole length.*—Average length of 3.6 mm.
- *b. Petiole color.*—Pantone Green Banana 14-0434.
- *c. Petiole surface texture.*—Smooth.

FLOWERS

Flower arrangement: Arranged alternately along branch.

Fragrance: Faint fragrance.

Flower shape: Urceolate.

Flower length: Average length of 9 mm.

Flower buds: 50% flower bud break February 24 in Lowell, Oreg.

Immature flower color: Pantone Holly Berry 17-1633.

Flowering cluster: Loose.

Flowering period: First flowers appear at the beginning of April through the end of May.

Number of flowers: Average of 6 to 7 flower buds per fruiting twig. 1 per twig would be low, while 7 flower buds per twig would be high.

Stigma location: Average of 0.3 mm beyond the lip of the corolla.

Corolla:
- *a. Corolla length.*—Average of 5.7 mm.
- *b. Corolla diameter.*—Average of 6.3 mm.
- *c. Corolla color.*—Pantone Pastel Parchment 11-0603.

*d. Corolla surface texture.*—Smooth.
*e. Corolla aperture.*—Average of 3.2 mm.

Calyx:
*a. Calyx diameter.*—Average of 4.3 mm.
*b. Calyx color.*—Pantone Tarragon 15-0326, tips of lobes Pantone Holly Berry 17-1633 to Pantone Malaga 17-1723.
*c. Calyx surface texture.*—Smooth.

Flower pedicel:
*a. Pedicel length.*—Average of 5 mm.
*b. Pedicel color.*—i. Lower side: Pantone Lettuce Green 13-0324. ii. Upper side: Pantone Holly Berry 17-1633.
*c. Pedicel surface texture.*—Smooth.

Flower peduncle:
*a. Peduncle length.*—Average of 10 mm.
*b. Peduncle color.*—i. Lower side: Pantone Lettuce Green 13-0324. ii. Upper side: Pantone Holly Berry 17-1633.
*c. Peduncle surface texture.*—Smooth.

Style length: Average of 6.5 mm.
Pistil color: Pantone Mellow Green 12-0426.

Anther:
*a. Anther length.*—Average of 3.5 mm.
*b. Anther color.*—Pantone Red Ochre 18-1442.

Pollen:
*a. Pollen staining.*—95% fertile, staining using 2% acetocarmine stain.
*b. Pollen abundance.*—High.
*c. Pollen color.*—Pantone Pale Banana 12-0824.

Self compatibility: Moderate to high, 80-90% of self pollinated flowers reaching maturity.

FRUIT

Mean harvest date first pick: July 16.
Mean harvest date last pick: August 7.

Calyx:
*a. Calyx aperture.*—Average of 6.2 mm.
*b. Calyx lobes.*—Small, flat, 5-lobed.
*c. Calyx depth.*—Average of 1.73 mm.

Berry cluster: Loose.
Immature berry color: Pantone Green Banana 14-0434.
Fruit ripening: a. 5% blue on July 1. b. 25% blue on July 7. c. 50% blue on July 16.
Berry pedicel length: Average of 9.5 mm.
Berry peduncle length: Average of 13.76 mm.
Berries per cluster: Average of 5-7 berries per cluster.
Berry detachment: Medium detachment force.
Berry weight: Average of 1.49 g.
Berry height: Average of 11.77 mm.
Berry width: Average of 16.56 mm.
Berry shape: Round, oblate.

Berry color:
*a. Berry skin color on plant.*—Pantone Gray Dawn 14-4106.
*b. Berry skin color after harvest.*—Pantone Velvet Morning 18-3927.
*c. Berry skin color after polishing.*—Pantone Deep Navy 19-4013.

Berry wax: Medium to heavy wax, moderately persistent.
Berry flesh color: Pantone Citron 12-0524.
Pedicel scar: Medium dry scar with an average diameter of 2.98 mm.
Berry firmness: Medium firmness.
Berry flavor: Mildly sweet.
Berry texture: Smooth.
Seeds per berry: Average of 24 seeds per fruit.

SEEDS

Seed color: Pantone Cedar Wood 17-1525.
Seed length: Average of 1.98 mm.
Seed width: Average of 1.28 mm.
Seed weight: Average of 0.5 mg.

What is claimed is:

1. A new and distinct variety of blueberry plant named 'ZF06-079', substantially as illustrated and described herein.

* * * * *